(12) United States Patent
Morrey et al.

(10) Patent No.: US 9,687,586 B2
(45) Date of Patent: Jun. 27, 2017

(54) HIP IMPLANT

(75) Inventors: Bernard Morrey, Fayetteville, TX (US); Kai-Nan An, Rochester, MN (US); Andrew Thoreson, Kenyon, MN (US); Qingshan Chen, Rochester, MN (US); Xinyuan David Wang, East Lyme, CT (US); James Zhiming Jiang, Burlington, MA (US)

(73) Assignee: Excera Orthopedics, Inc., Newton, MA (US)

( * ) Notice: Subject to any disclaimer, the term of this patent is extended or adjusted under 35 U.S.C. 154(b) by 102 days.

(21) Appl. No.: 13/640,222

(22) PCT Filed: Mar. 24, 2011

(86) PCT No.: PCT/US2011/029809
§ 371 (c)(1),
(2), (4) Date: Oct. 9, 2012

(87) PCT Pub. No.: WO2011/126757
PCT Pub. Date: Oct. 13, 2011

(65) Prior Publication Data
US 2013/0030543 A1   Jan. 31, 2013

Related U.S. Application Data

(60) Provisional application No. 61/322,750, filed on Apr. 9, 2010.

(51) Int. Cl.
*A61F 2/32*       (2006.01)
*A61L 27/30*      (2006.01)
(Continued)

(52) U.S. Cl.
CPC .......... *A61L 27/306* (2013.01); *A61F 2/3601* (2013.01); *A61F 2/3662* (2013.01);
(Continued)

(58) Field of Classification Search
USPC ....................... 623/22.11–22.16, 22.4–23.47
See application file for complete search history.

(56) References Cited

U.S. PATENT DOCUMENTS 3,965,490 A   6/1976   Murray et al.
4,608,055 A   8/1986   Morrey et al.
(Continued)

FOREIGN PATENT DOCUMENTS

CN       2118508       10/1992
CN      201029959      3/2008
(Continued)

OTHER PUBLICATIONS

International Search Report, dated Dec. 26, 2011, in corresponding in International Application No. PCT/US2011/029809.
(Continued)

*Primary Examiner* — Yashita Sharma
(74) *Attorney, Agent, or Firm* — Meunier Carlin & Curfman LLC (57) ABSTRACT

Provided herein is a femoral component of a hip implant device, comprising a neck having a central axis; and a body distal to the neck and having a tapered portion, wherein the body has a largest cross section perpendicular to the neck central axis, the largest cross section perpendicular to the neck central axis having a maximum height dimension and a maximum width dimension, wherein the maximum width dimension is 18.5 mm or less. The hip implant can optionally be used in patients of Asian descent.

21 Claims, 9 Drawing Sheets

(51) Int. Cl.

| | | |
|---|---|---|
| *A61F 2/36* | (2006.01) | |
| *A61L 27/56* | (2006.01) | |
| *C23C 4/06* | (2016.01) | |
| *C23C 4/073* | (2016.01) | |
| *A61F 2/46* | (2006.01) | |
| *A61F 2/30* | (2006.01) | |

(52) U.S. Cl.
CPC ............... *A61L 27/56* (2013.01); *C23C 4/06* (2013.01); *C23C 4/073* (2016.01); *A61F 2/4607* (2013.01); *A61F 2002/30011* (2013.01); *A61F 2002/3092* (2013.01); *A61F 2002/30176* (2013.01); *A61F 2002/30616* (2013.01); *A61F 2002/30667* (2013.01); *A61F 2002/30706* (2013.01); *A61F 2002/30795* (2013.01); *A61F 2002/30807* (2013.01); *A61F 2002/3678* (2013.01); *A61F 2002/3686* (2013.01); *A61F 2310/00023* (2013.01); *A61F 2310/00407* (2013.01); *A61L 2430/24* (2013.01)

(56) References Cited

U.S. PATENT DOCUMENTS

| | | | |
|---|---|---|---|
| 4,657,551 A | | 4/1987 | Ecke |
| 4,705,520 A | | 11/1987 | Ahrens |
| 4,865,608 A | * | 9/1989 | Brooker, Jr. ............... 623/23.29 |
| 5,156,627 A | | 10/1992 | Amstutz et al. |
| 5,342,366 A | | 8/1994 | Whiteside et al. |
| 5,507,833 A | | 4/1996 | Bohn |
| 5,591,233 A | | 1/1997 | Kelman et al. |
| 6,102,957 A | * | 8/2000 | Noble et al. ............... 623/23.35 |
| 6,312,473 B1 | | 11/2001 | Oshida |
| 6,319,286 B1 | * | 11/2001 | Fernandez .......... A61F 2/30734 623/16.11 |
| 7,060,102 B2 | | 6/2006 | Thompson et al. |
| 7,611,541 B2 | * | 11/2009 | Thompson et al. ....... 623/23.35 |
| 2002/0120344 A1 | | 8/2002 | Meulink et al. |
| 2002/0133234 A1 | | 9/2002 | Sotereanos |
| 2002/0133324 A1 | | 9/2002 | Weaver et al. |
| 2003/0130741 A1 | | 7/2003 | McMinn |
| 2004/0002759 A1 | | 1/2004 | Ferree |
| 2005/0010232 A1 | | 1/2005 | Crofford |
| 2005/0159821 A1 | | 7/2005 | Thompson et al. |

FOREIGN PATENT DOCUMENTS

| | | |
|---|---|---|
| CN | 101496749 | 8/2009 |
| EP | 0700670 | 3/1996 |
| EP | 1240879 | 9/2002 |
| EP | 1614401 | 1/2006 |
| FR | 2784576 | 4/2000 |
| JP | 11341 | 1/1999 |
| JP | 2002/330983 | 11/2002 |
| JP | 2007/518531 | 7/2007 |
| WO | 9812994 | 4/1998 |
| WO | 2005/072231 | 9/2005 |

OTHER PUBLICATIONS

International Preliminary Report on Patentability, dated Oct. 9, 2012, in corresponding in International Application No. PCT/US2011/029809.
Written Opinion of the International Searching Authority, dated Dec. 26, 2011, in corresponding in International Application No. PCT/US2011/029809.
"Short Hip Stem: Evolving the State of Arthroplasty," Aug. 2008, Aesculap Implant Systems, Inc., Center Valley, PA.
Morrey, B.F., "A conservative femoral replacement for total hip arthroplasty: a prospective study," J. Bone and Joint Surg.-British Volume, Sep. 2000, vol. 82-B, No. 7: 952-958.
Morrey, Bernard F., M.D., "Short-Stemmed Uncemented Femoral Component for Primary Hip Arthroplasty," Clinical Orthopaedics and Related Research, Dec. 1989, No. 249:169-175.
Noble, P.C. et al., "The anatomic basis of femoral component design," Clinical Orthopaedics and Related Research, Oct. 1988, No. 235: 148-165.
Lausten, G.S. et al., "Measurement of anteversion of the femoral neck," J. Bone and Joint Surg.-British Volume, Mar. 1989, vol. 71-B, No. 2: 237-239.
Yehyawi, T.M. et al., "Variances in sagittal femoral shaft bowing in patients undergoing KNA," Clinical Orthopaedics and Related Research, Nov. 2007, No. 464: 99-104.
Extended Search Report, dated Feb. 7, 2014, received in connection with corresponding European Application No. 11766399.7.
Search Report, dated Jan. 16, 2014, received in connection with corresponding Singapore Application No. 201207478-7.
Written Opinion, dated Jan. 16, 2014, received in connection with corresponding Singapore Application No. 201207478-7.
Office Action, dated Dec. 26, 2014, received in connection with corresponding JP Application No. 2013-503775. (Original and English Translation).
Examination Report issued by the Intellectual Property Office of Singapore in application No. 201207478-7 dated Sep. 13, 2015.
Second Office Action dated Feb. 10, 2015 issued in Chinese Application No. 201180020431.9.
Third Office Action dated Jul. 16, 2015 issued in Chinese Application No. 201180020431.9.
Office Action dated Dec. 22, 2014, issued in Japanese application No. 2013-503775.
Search Report dated Jul. 2, 2015, issued in Chinese Application No. 201180020431.9.

* cited by examiner

HIP IMPLANT

CROSS-REFERENCE TO RELATED APPLICATIONS

This application claims the benefit of U.S. Patent Application No. 61/322,750 filed on Apr. 9, 2010, which is incorporated herein by reference in its entirety.

TECHNICAL FIELD

This document relates to hip implant devices and related surgical methods.

BACKGROUND

Total hip replacement (THR) is a surgical procedure in which various components of a patient's hip joint are replaced with artificial components in order to restore functionality of the patient's hip.

In one common THR procedure, an artificial acetabular cup is implanted in place of the patient's natural acetabulum, and a femoral prosthesis is implanted into the patient's femur. The femoral prosthesis has a head that engages the artificial acetabular cup to allow the femoral prosthesis/ acetabular cup combination to function much like the natural hip joint. However, the ability of an artificial hip joint to function like the patient's natural hip joint depends on how well the components of the artificial hip fit when implanted into a particular patient.

SUMMARY

Provided are femoral components for hip implant devices and related surgical methods. One example femoral component comprises a neck having a central axis and a body distal to the neck. The body has a tapered portion and a largest cross section perpendicular to the neck central axis. The largest cross section perpendicular to the neck central axis has a maximum height dimension and a maximum width dimension, wherein the maximum height dimension is about 23.9 mm or less and can optionally be between about 20.3 mm and 23.9 mm. The maximum width dimension can be about 18.5 mm or less, and is optionally between about 15.7 mm and 18.5 mm.

In some aspects, the tapered portion is tapered from proximal to distal in the sagittal and coronal planes. The tapered portion can be further tapered in the lateral to medial in cross section.

Optionally, the body has an exterior surface and a porous surface coating is applied circumferentially to the surface of the body. The porous surface coating can be applied by plasma spray. The porous surface coating can optionally comprise metal such as, for example, titanium.

Another example femoral component of a hip implant device comprises a neck and a body distal to the neck. The body has a tapered portion and a stem portion having a distal tip and a central axis. The length of the body as measured from the medial junction of the neck and body along an axis parallel to the central axis of the stem portion can be about 125 mm or less. For example, the length of the body can be, or can be less than, about 125, 120, 115, 110, 105, 100, 95, 90, 85 or 80 mm, or any value there between.

The body can further comprise a lateral humped portion. The device can have a triple taper geometry. In this triple taper geometry, the tapered portion is tapered proximal to distal in the sagittal and coronal planes and in the lateral to medial in cross section. The stem portion can be optionally positioned in the diaphysis of a femur and does not contact the cortex of the intramedullary canal.

In some aspects, the body has an exterior surface and the femoral component further comprises a porous surface coating applied circumferentially to the surface of the body. The porous surface coating can be located proximal to the stem portion and can optionally coat the humped portion. The porous surface coating can be applied by plasma spray.

In yet another example, a femoral component of a hip implant device comprises a neck and a body distal to the neck. The body has a tapered portion and a stem portion having a distal tip. The stem portion is proportioned such that the stem portion has no substantial contact with the intramedullary canal cortex when the femoral component is implanted in a femur. The body can optionally comprise a lateral humped portion.

Optionally, the stem portion has no contact with the intramedullary canal cortex when the femoral component is implanted in a femur. Optionally, the stem portion has only tangential contact with the intramedullary canal cortex when the femoral component is implanted in a femur. In some examples, the stem portion has a central axis and the length of the body as measured from the medial junction of the neck and body along a axis parallel to the central axis of the stem portion is about 125 mm or less. For example, the length of the body can be, or can be less than, about 125, 120, 115, 110, 105, 100, 95, 90, 85 or 80 mm, or any value there between.

The tapered portion can be tapered proximal to distal in the sagittal and coronal planes and can be further tapered in the lateral to medial in cross section. The tapered portion can thereby have a triple tapered geometry.

Optionally, the body has an exterior surface and the femoral component further comprises a porous surface coating applied circumferentially to the surface of the body. The porous surface coating can be applied by plasma spray. The porous surface coating can optionally comprise metal such as, for example, titanium.

An example method of implanting a femoral component during hip surgery comprises providing a femoral component comprising a body and implanting the femoral component into the femur of a patient. In the example method, a portion of the body of the femoral component enters the intramedullary canal of the patient and the portion that enters the intramedullary canal does not substantially contact the cortex of the intramedullary canal when implanted in the subject's femur. Optionally, the portion of the body that enters the intramedullary canal has no contact with the cortex of the intramedullary canal. Optionally, the portion of the body that enters the intramedullary canal has only tangential contact with the cortex of the intramedullary canal. The femoral component is optionally substantially fixed in the patient's femur in the metaphysis of the femur. The patient is optionally of Asian descent.

Another example method comprises providing a femoral component comprising a body, wherein the body comprises a distal stem portion and implanting the femoral component into the femur of a patient during a surgical procedure. In the example method, a portion of the body, including the distal stem portion, of the femoral component enters the intramedullary canal of the patient and the distal stem portion does not substantially contact the cortex of the intramedullary canal when the femoral component is implanted in the subject's femur. Optionally, the portion of the body that enters the intramedullary canal has no contact with the cortex of the intramedullary canal. Optionally, the portion of the body that enters the intramedullary canal has only tangential contact with the cortex of the intramedullary canal. The femoral component is optionally substantially fixed in the patient's femur in the metaphysis of the femur. The patient is optionally of Asian descent.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The design of an artificial hip (e.g. the acetabular cup, and the femoral prosthesis) is complicated by significant variation in hip and femur anatomy. The anatomy of the hip and femur are known to vary based on race and on disease type. For example, the femur of an individual of Asian descent with developmental dysplasia of the hip (DDH) may have a larger femoral neck anteversion (FNA) angle and/or a narrower intramedullary canal than that of an individual without a hip disease or of an individual with another type of hip disease, such as osteoarthritis. Patients, such as those of Asian decent, can also have characteristics such as bowed and small femurs.

As a consequence, the components of an artificial hip designed for Caucasian osteoarthritis patients do not function optimally when implanted in an individual with another disease type or in an individual of another race. In addition, the anatomical abnormalities of a patient with DDH (e.g. larger FNA angle or narrower intramedullary canal) increase the technical difficulty of performing a THR procedure in a patient with DDH. Poor functioning of an artificial hip implant may include an increased risk of intra-operative fracture, increased pain, imbalanced gait, micromotion and loosening between implant components and the surrounding bone, insufficient support for the implant components, poor initial press fit, increased rate of implant failure, decreased patient mobility, and poor artificial hip stability.

Provided herein are hip implant devices and related surgical methods. The devices and methods can optionally be used in patients of Asian descent. For example, the devices and methods can be used in Asian patients having DDH or other conditions of the hip, such as osteoarthritis, for which hip surgery is indicated.

Figure 1:
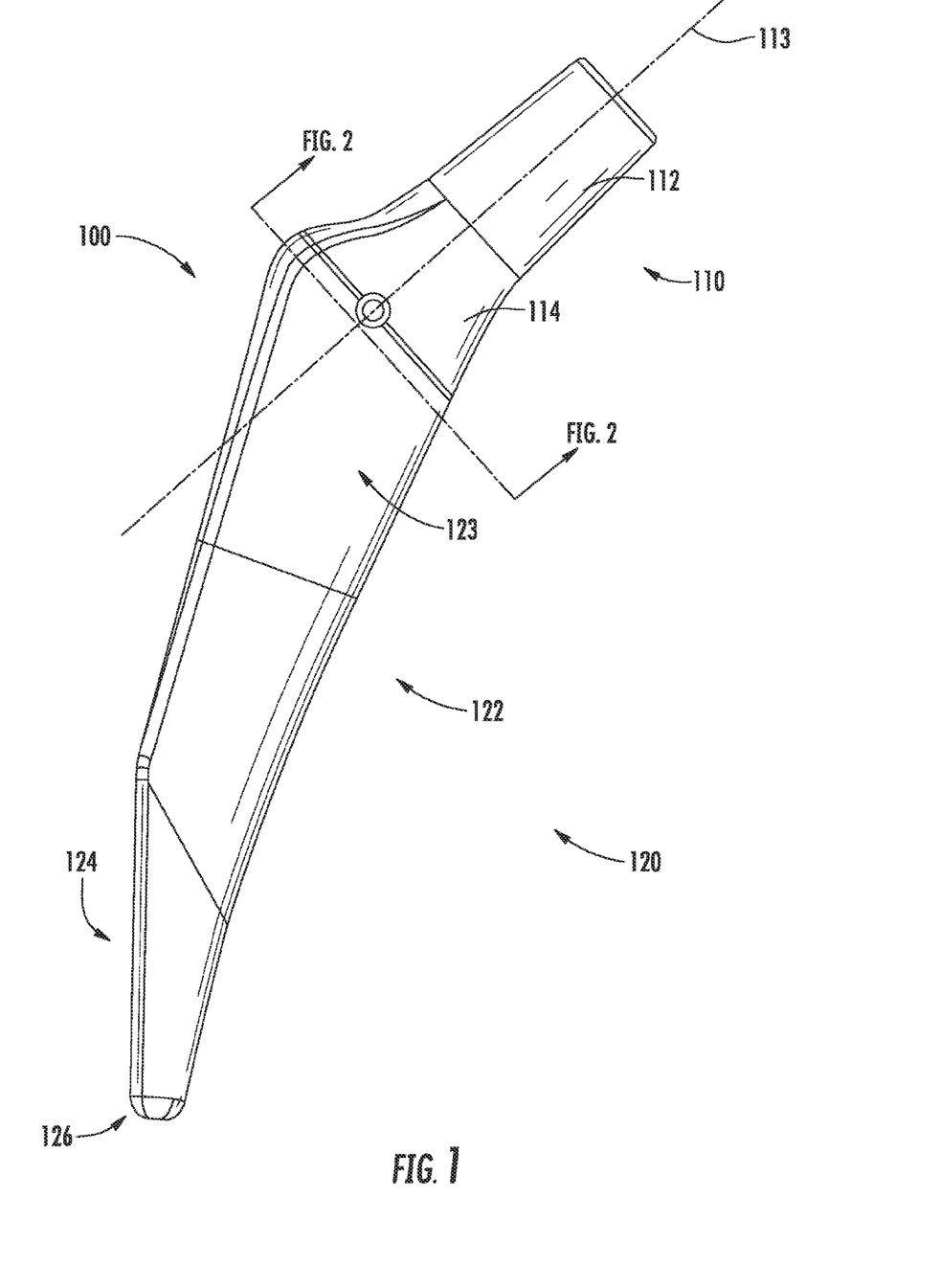
FIG. 1 is a side view of a stemless hip implant, in accordance with some embodiments.
Figure 2:
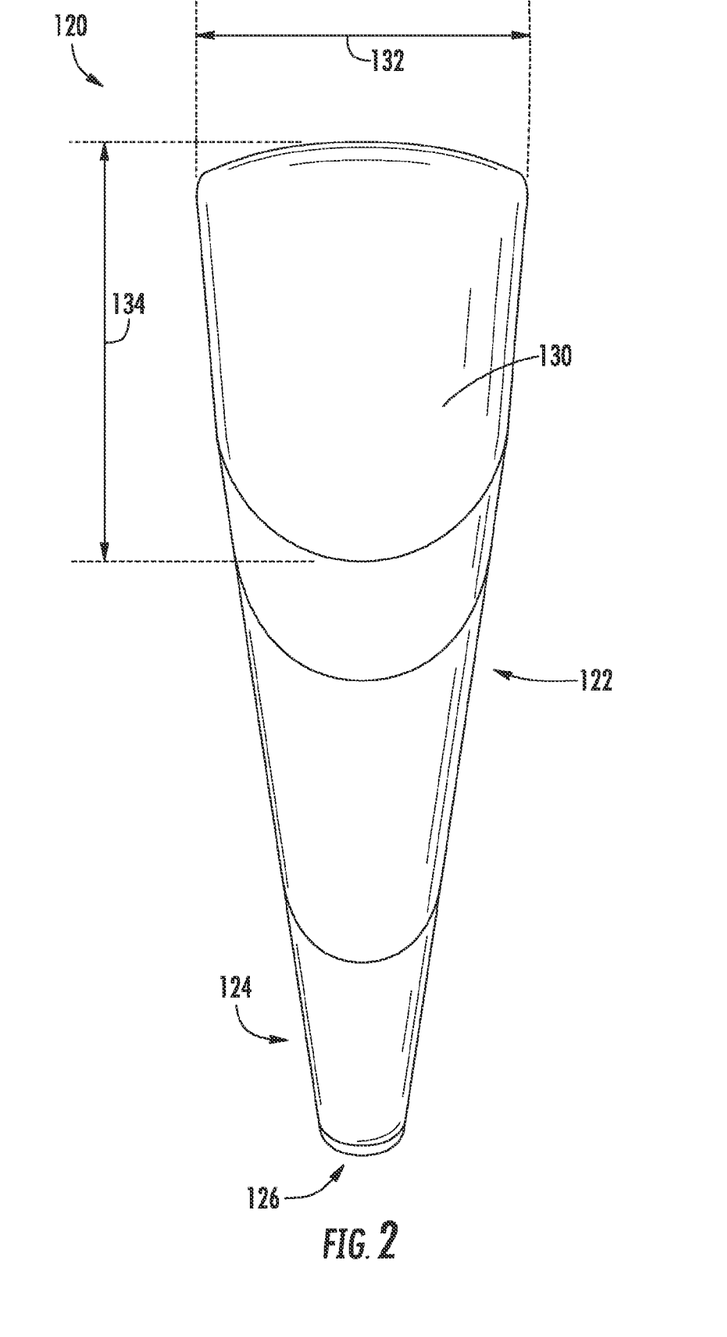
FIG. 2 is a cross-section view of the stemless hip implant of FIG. 1.

Referring now to FIG. 1-2, some embodiments of a hip implant system include a femoral implant 100 configured to be implanted in a femur. The femoral implant 100 can include a neck portion 110 located proximally on the femoral implant 100 and a distally located body 120. The femoral implant 100 can be configured such that at least a portion of the distally located body 120 can be implanted inside a cavity that is surgically formed in a femur and the neck portion 110 can receive a ball such that the ball and attached neck portion 110 can be positioned inside an acetabular cup. In this configuration, the femoral implant 100 can be used to restore hip function to an individual whose hip has been damaged or is not functioning properly such that hip surgery is indicated (e.g., due to mechanical damage, disease, congenital conditions, developmental conditions, old age, and the like). The neck portion 110 can include a shaft 112 for receiving a replacement ball and a transition portion 114 that serves to transition between the shaft 112 and the body 120. In some embodiments, the shaft 112 defines a central axis 113. In one example, the shaft 112 is a tapered, cylindrical shaft with the central axis 113.

In some embodiments, the femoral implant 100 can be configured such that use of the femoral implant in an individual is not limited based on physiologic factors of the individual such as small stature, a bowed femur, and the like. For example, devices described herein can be used in Asian subjects. In some examples, Asian subjects may have DDH, decreased femoral head offset, increased anteversion angle, increased femoral bowing, and the like. In some examples, the femoral implant 100 can include the body 120 with a cross-section 130 that is small enough to be implanted in individuals with femurs that have a smaller cross-sectional area. In another example, the body 120 can have an overall length (described in greater detail in connection with FIG. 5) that is short enough, such that when the implant 100 is placed within a surgically prepared space within a femur, the body 120 is located at least partially within a surgically formed cavity in the metaphysis, but does not substantially enter the intramedullary canal of the femoral diaphysis. In this so called stem-less design, since the body 120 may not substantially enter the femoral diaphysis, the implant 100 is not dependent on the morphology of the femoral diaphysis and can be used in conjunction with a wide range of femur morphologies. In these cases, the metaphysis it the primary site of fixation of the device and the diaphysis can be optionally ignored for purposes of surgical planning and fitting of the device in a patient. Moreover, the implant 100 can advantageously be used in individuals of smaller stature, individuals with unusual morphologies such as bowed femurs, and the like.

Referring now to TABLE 1, differences exist between the Caucasian and Asian populations that influence the fit of femoral implants. TABLE 2 shows that there are significant differences in parameters that differentiate Asian DDH and Asian non-DDH patients. Pathology leads to different femur geometry between DDH and non-DDH, in particular to different anteversion angle, that influence the fit of implants. Furthermore, computer simulation indicates that current western hip implants, including the implants of top global brands, do not fit appropriately into the femur of 20% Asian patients. In some embodiments, a stemless implant 100 (e.g., an implant 100 where the body 120 does not substantially enter the intramedullary cavity or canal of the femoral diaphysis) may be more appropriate than traditional femoral implants.

TABLE 1

Exemplary Anatomical Features of Asian and Caucasian Populations

| Parameter (CT Measurement) | Asian | Caucasian |
| --- | --- | --- |
| Femoral head offset | 34.9 ± 8.3 (n = 67) | 43 ± 6.8 (n = 200) |
| Neck shaft angle | 131.5 ± 7.1 (n = 67) | 127 ± 5.5 (n = 8074) |
| Anteversion angle | 17.3 ± 9.3 (n = 67) | 13.3 ± 7.4 (n = 30) |
| Bowing angle | 6.0 ± 2.2 (n = 58) | 4.9 ± 2.7 (n = 145) |

TABLE 2

Exemplary Anatomical Features of Asian DDH and non-DDH Populations

| Parameter (CT Measurement) | Asian | Caucasian |
| --- | --- | --- |
| Femoral Head Offset | 32.6 ± 7.5 (n = 37) | 37.7 ± 8.6 (n = 30) |
| Neck Anteversion Angle | 19.2 ± 10.6 (n = 37) | 15.0 ± 6.9 (n = 30) |

The femoral implant 100 can include a proximal portion 122 of the body 120, as will be described in greater detail below, is tapered in three directions to allow for changes in dimension of the femur. In some embodiments, a region 123 can include a surface preparation to encourage a strengthened interface between the implant 100 and the femur it is to be implanted in. For example, the region 123 located in the proximal portion 122 can include a porous coating applied circumferentially to the surface of the region 123. In some embodiments, the porous region can be applied via a plasma coating process. This process advantageously can add a porous surface (to encourage bone ingrowth and attachment) without substantially modifying or weakening the implant 100. In some embodiments, the plasma coating can include any biocompatible material having characteristics that allow the applied coating to serve its function. For example, the coating can include titanium alloys, alloys of cobalt and chromium, and the like. The body 120 can include a distal region 124 that exists at an angle relative to the proximal portion 122. The body 120 can include a distal tip portion 126. In some embodiments, the tip portion 126 can be configured in a blunt configuration, such as having a width of 5 mm with edges that have a radius of 2 mm. In some embodiments, a blunt distal tip portion 126 can advantageously affect manufacturing.

Referring now to FIG. 2, the implant 100 can contain a planar cross-section 130 in the body 120 that is perpendicular to the axis 113 (FIG. 1). As depicted, the cross-section 130 represents substantially the largest cross-sectional area within the body that is perpendicular to the axis 113. Portions of the body 120 (e.g., the cross-section 130, the region 123, portions of the proximal portion 122, and the like) can be configured to provide a friction fit between the implant 100 and at least a portion of the metaphysis of a femur. The cross-section 130 can include a width 132 and a height 134 that can define the cross-section 130. In some embodiments, the height 134 and width 132 are small enough such that the implant 100 can be advantageously implanted in individuals of smaller stature (e.g., members of the Asian populations, younger individuals, individuals with smaller femurs, and the like). For example, the implant 100 can be available in multiple sizes to accommodate differently sized femurs. TABLE 3 lists some example, or exemplary combinations of height 134 and width 132 of the cross-section 130.

TABLE 3

EXEMPLARY STEMLESS HIP IMPLANT DEVICE CROSS SECTION DIMENSIONS

| Device # | Height (mm) | Width (mm) |
| --- | --- | --- |
| 1 | 20.3 | 15.7 |
| 2 | 21.9 | 17.2 |
| 3 | 23.4 | 19.3 |
| 4 | 26 | 21.5 |

In some examples, the cross-section 130 can include a height 134 that is about 23.9 millimeters (mm) or less and a width 132 that is about 18.5 millimeters (mm) or less. In some examples, the height 134 can be any value between 20.3 mm and 23.9 mm. For example, the height can be 20.3, 20.4, 20.5, 20.6, 20.7, 20.8, 20.9, 21.0, 21.1, 21.2, 21.3, 21.4, 21.5, 21.6, 21.7, 21.8, 21.9, 22.0 22.1, 22.2, 22.3, 22.4, 22.5, 22.6, 22.7, 22.8, or 22.9 mm. In some examples, the width 132 can be any value between 15.7 mm and 18.5 mm. For example, the width can be 15.7, 15.8, 15.9, 16.0, 16.1, 16.2, 16.3, 16.4, 16.5, 16.6, 16.7, 16.8, 16.9, 17.0 17.1, 17.2, 17.3, 17.4, 17.5, 17.6, 17.7, 17.8, 17.9, 18.0 18.1, 18.2, 18.3, 18.4, or 18.5 mm. It should be appreciated that other combinations of height 134 and width 132 can be used. For example, an implant 100 can be chosen by a surgeon depending on pre-surgical inspections (e.g., X-rays, MRIs, and the like), information obtained during the surgical procedure (e.g., the size of the cavity created in the femur during resection), and the like.

The various components of the implant 100 as described above may be constructed out of any biocompatible material having characteristics that allow the implant 100 to serve its function. Various biocompatible metals, plastics, and ceramics may be used to make the components of the implant 100. For example, the neck 110, body 120, and the like, may be made out of any high strength biocompatible material. Examples include alloys of cobalt and chromium, titanium alloys, and stainless steel alloys. In an exemplary embodiment, the acetabular cup may be a metal backed acetabular cup with an interior surface made of a biocompatible wear-resistant material, such as ultrahigh molecular weight polyethylene.

The implant 100 according to one of the exemplary embodiments described above may be implanted using a number of surgical techniques. Examples of acceptable surgical techniques include the posterior, lateral, anterolateral and anterior approaches, and trochanter osteotomy. In addition, double incision, minimally invasive, and computer guided surgical techniques may be employed. Various surgical techniques and surgical instruments that may be used in the implantation of the components of an artificial hip are taught in U.S. Pat. No. 5,342,366 to Whiteside et al. and U.S. Pat. No. 5,507,833 to Bohn, both of which are incorporated herein by reference in their entireties.

Figure 3:
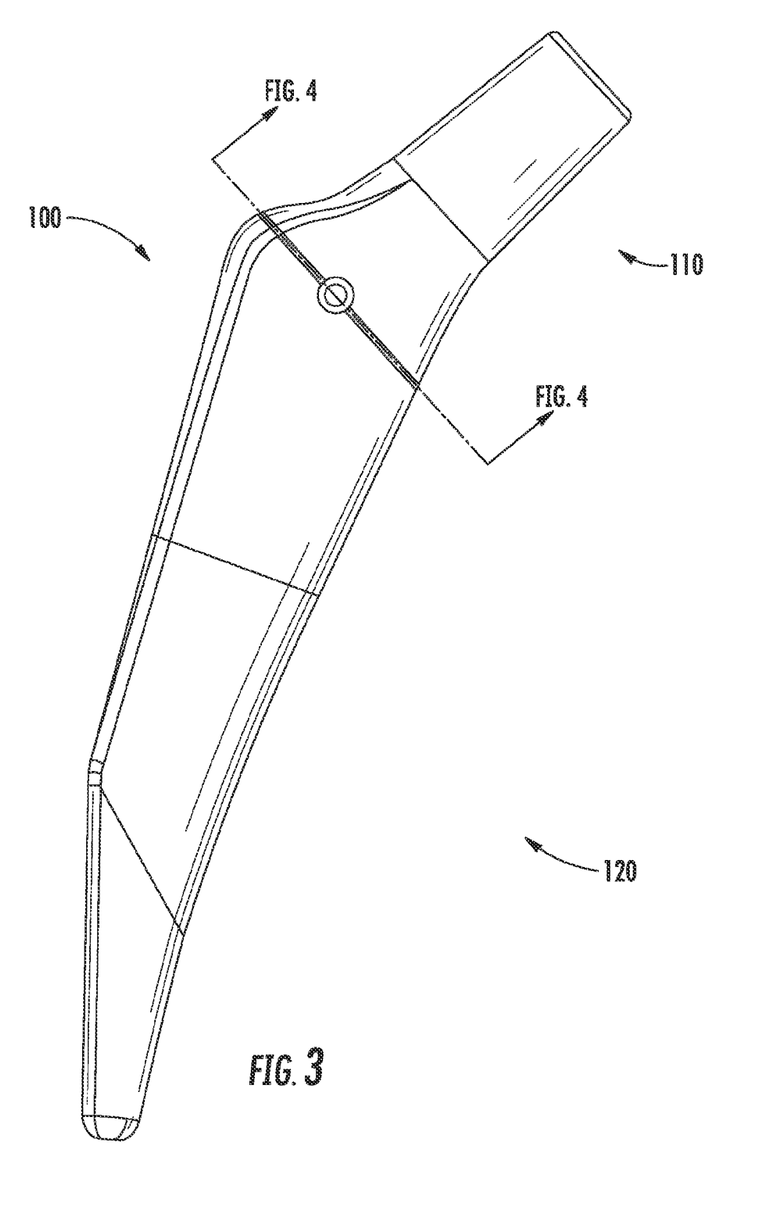
FIG. 3 is a side view of a stemless hip implant, in accordance with some embodiments.
Figure 4:
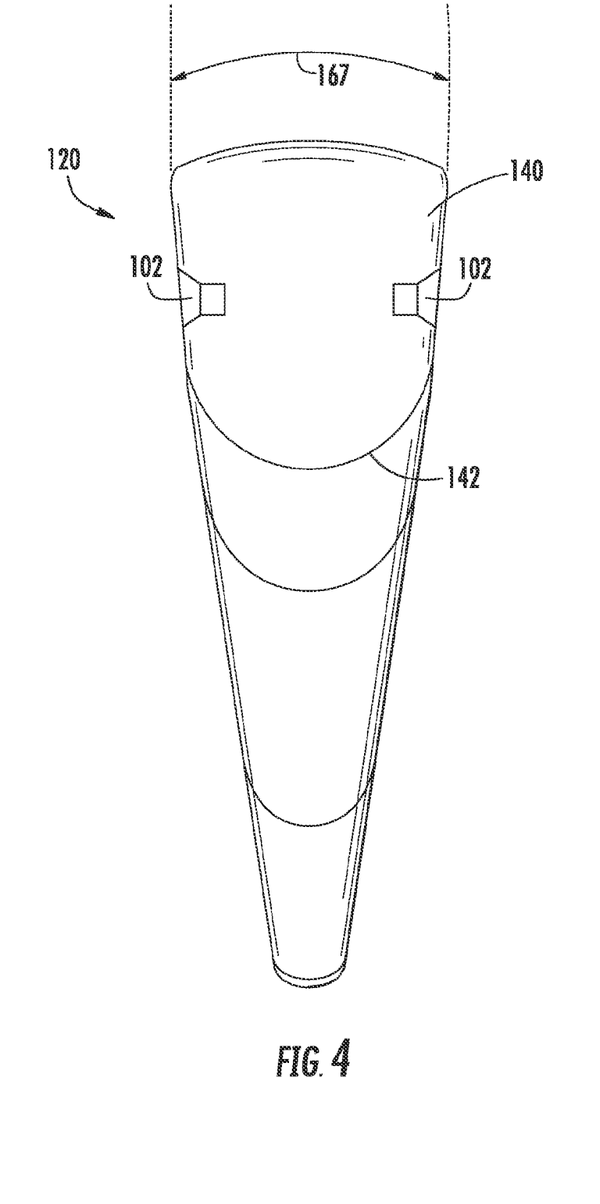
FIG. 4 is a cross-section view of the stemless hip implant of FIG. 3.

Referring now to FIGS. 3-4, the implant 100 can include a cross-section 140 substantially at an interface between the neck portion 110 and the body 120. Briefly, in use, when the implant 100 is implanted within a surgically prepared cavity within a femur, the cross-section 140 represents the cross-section that can be substantially flush with the remaining proximal portion of the femur. In these embodiments, the cross-section 140 can be smaller than the cross-section 130 and the cross-section 140 may not provide a friction fit between the implant 100 and the cortex of a femur, thus advantageously minimizing stress on the proximal edge of the surgically altered femur.

In some embodiments, the implant 100 can include orifices 102 located near the interface between the neck portion 110 and the body 120. In use, surgical tools can be inserted into the orifices 102 and used to assist in placement of the implant 100 within a femur (e.g., to supply additional leverage, to assist in alignment of the implant 100 within a femur, and the like).

Figure 5:
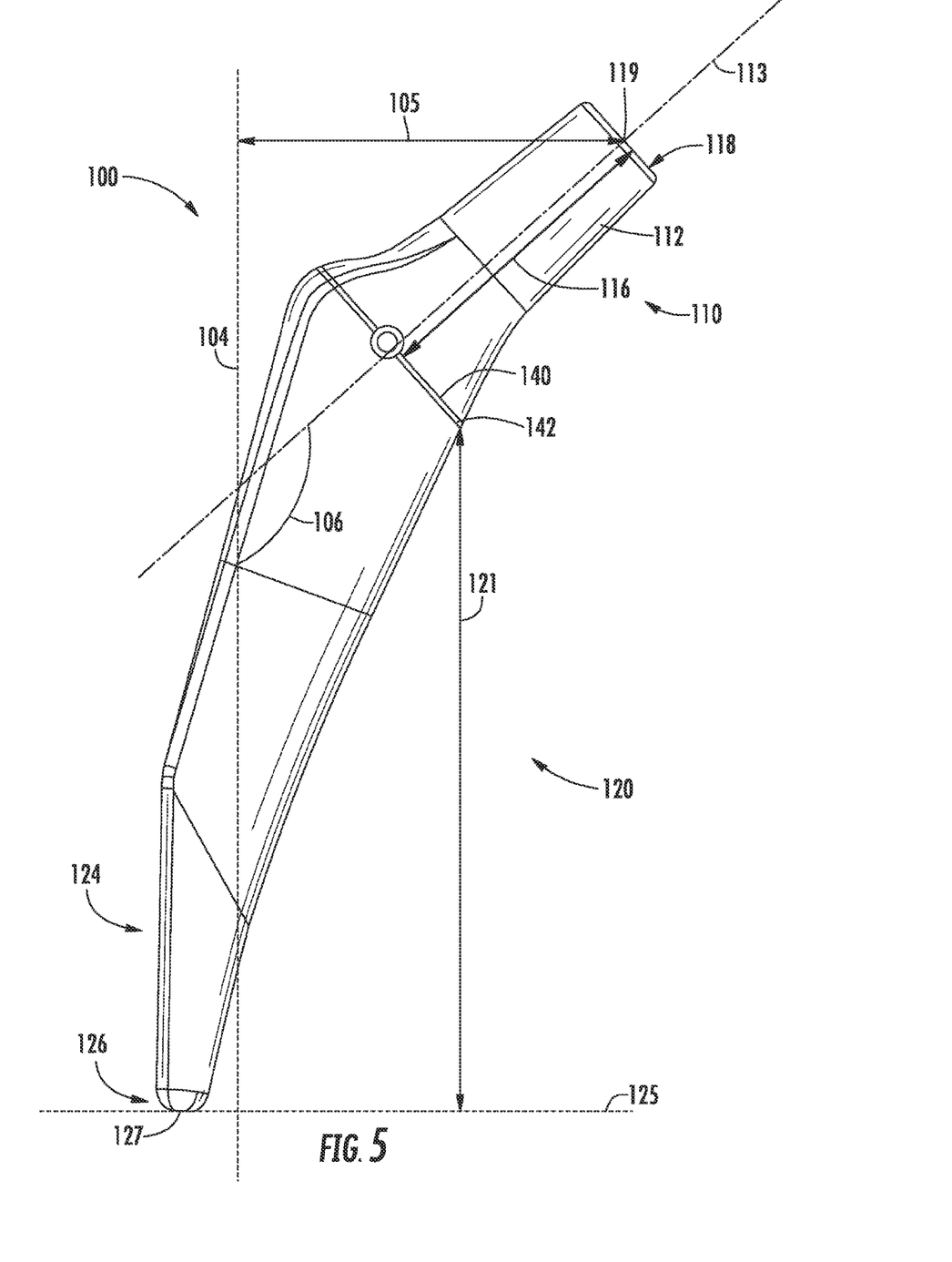
FIG. 5 is a side view of a stemless hip implant, in accordance with some embodiments.

Referring now to FIG. 5, the implant 100 can include features that allow the implant 100 to be implanted in femurs exhibiting a wide array of morphologies. For example, a shorter body 120 that does not substantially enter the femoral diaphysis can allow the implant 100 to be used in individuals with differently shaped femurs (e.g., femurs that are shorter in length, have smaller femoral head offsets, have larger bowing angles, have large anteversion angles, and the like). As described previously in connection with FIG. 4, the implant 100 can include a cross-section 140 that, when implanted in a surgically altered femur, is substantially flush with the outside edge of the femur. The implant 100 can include a neck offset 116 defined between the plane defined by the cross-section 140 and a proximal face 118 of the shaft 112. The implant 100 can be configured such that when the implant 100 is implanted in a surgically altered femur, particular dimensions can be measured from a central axis 104 defined by the femur (e.g., the central shaft of the femur). For example, a body offset 105 can exist between the axis 104 and a point 119 on the proximal face 118 of the shaft 112. The point 119 can be defined as the point where the axis 113 intersects the proximal face 118. In another example, the cross-section 140 can include a point 142 (see FIG. 4), on the lower portion of the cross-section 140. As such, a body length 121 can be defined as a length along a vector that is parallel to the central axis 104 and is bounded by the point 142 and a plane 125 that is perpendicular to the central axis 104 (and thus the body length 121) and contacts an outer tip 127 of the tip portion 126. Exemplary body lengths 121, neck offsets 116, and body offsets 105 can be found in TABLE 4. In some embodiments, an angle 106 of 132° can exist between the axes 104 and 113.

TABLE 4

EXEMPLARY STEMLESS HIP IMPLANT DEVICE DIMENSIONS

| Device # | Body Length (mm) | Neck Offset (mm) | Body Offset (mm) |
|---|---|---|---|
| 1 | 59.2 | 28.8 | 32.2 |
| 2 | 67.4 | 30.3 | 37.8 |
| 3 | 76.9 | 32.9 | 42.9 |
| 4 | 87 | 34 | 45.3 |

Figure 6A:
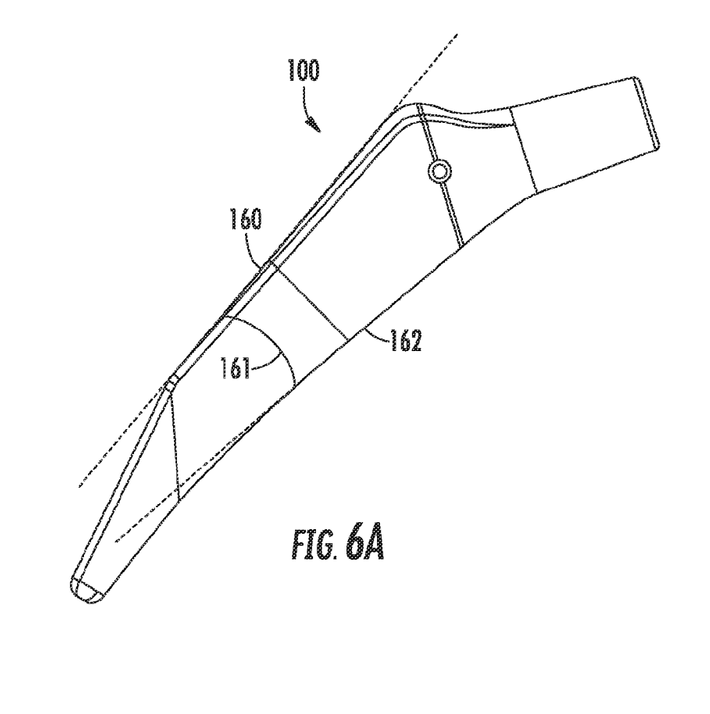
FIGS. 6A-6C are side, back, and cross-section views of the stemless hip implant of FIG. 5.
Figure 6B:
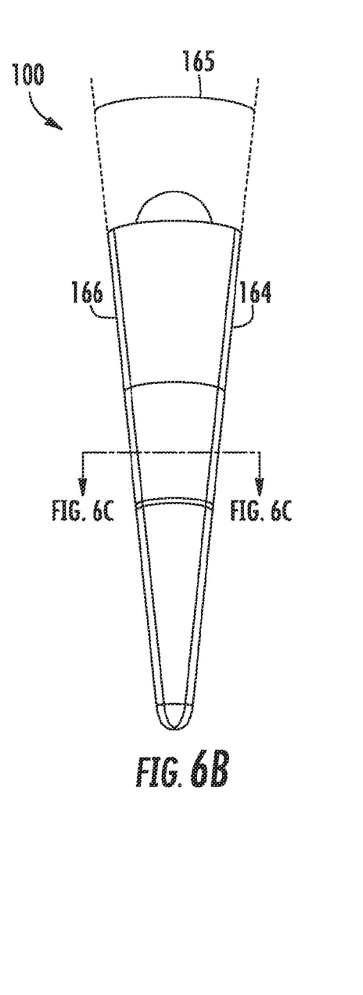
Figure 6C:
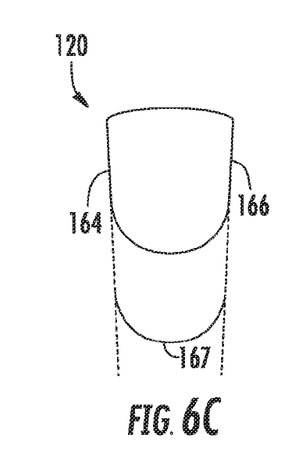

Referring now to FIGS. 6A-6C, the implant 100 can be configured with a triple taper design that can advantageously maximize the cross-sectional area of the body 120, while not substantially limiting the use of the implant 100 in femurs with differing morphologies. The triple taper design is configured such that the at least a portion of the body 120 is tapered in three planes. In some embodiments, the triple taper shaped body 120 is a dissimilar shape from the proximal femur, hence this triple taper shape can become stabilized into the irregular canal of the femur in a predictable manner, but with little depth of penetration. The femur canal is known to be tapered in these planes as well so incorporating tapers in the implant design can help increase filling of the metaphysis. In some embodiments, this triple taper design helps the implant 100 mate with femur morphologies that might not otherwise be possible with a non-tapered design. In some cases, implants without the advantageous tapering could require smaller cross-sectional areas to properly fit inside a femur, thus weakening the implant. These implants could also be limited by certain femur morphologies (e.g., bowing of the femur). FIGS. 6A-6C each depict one of the three tapers. FIG. 6A depicts the implant 100 in the coronal plane (when implanted in a femur) such that a lateral surface 160 and a medial surface 162 are visible. A taper angle 161 is defined between the lateral surface 160 and the medial surface 162 in the coronal plane. In some embodiments, the taper angle 161 is about 5.0°. FIG. 6B depicts the implant 100 in the sagittal plane (when implanted in a femur) such that an anterior surface 164 and a posterior surface 166 are visible. A taper angle 165 is defined between the anterior surface 164 and the posterior surface 166 in the sagittal plane. In some embodiments, the taper angle 165 is about 12.0°. FIG. 6C depicts a cross-section of the implant 100 in the transverse plane (when implanted in a femur) such that the anterior surface 164 and the posterior surface 166 are visible. A taper angle 167 is defined between the anterior surface 164 and the posterior surface 166 in the transverse plane. In some embodiments, the taper angle 167 is about 8.5°.

Figure 7:
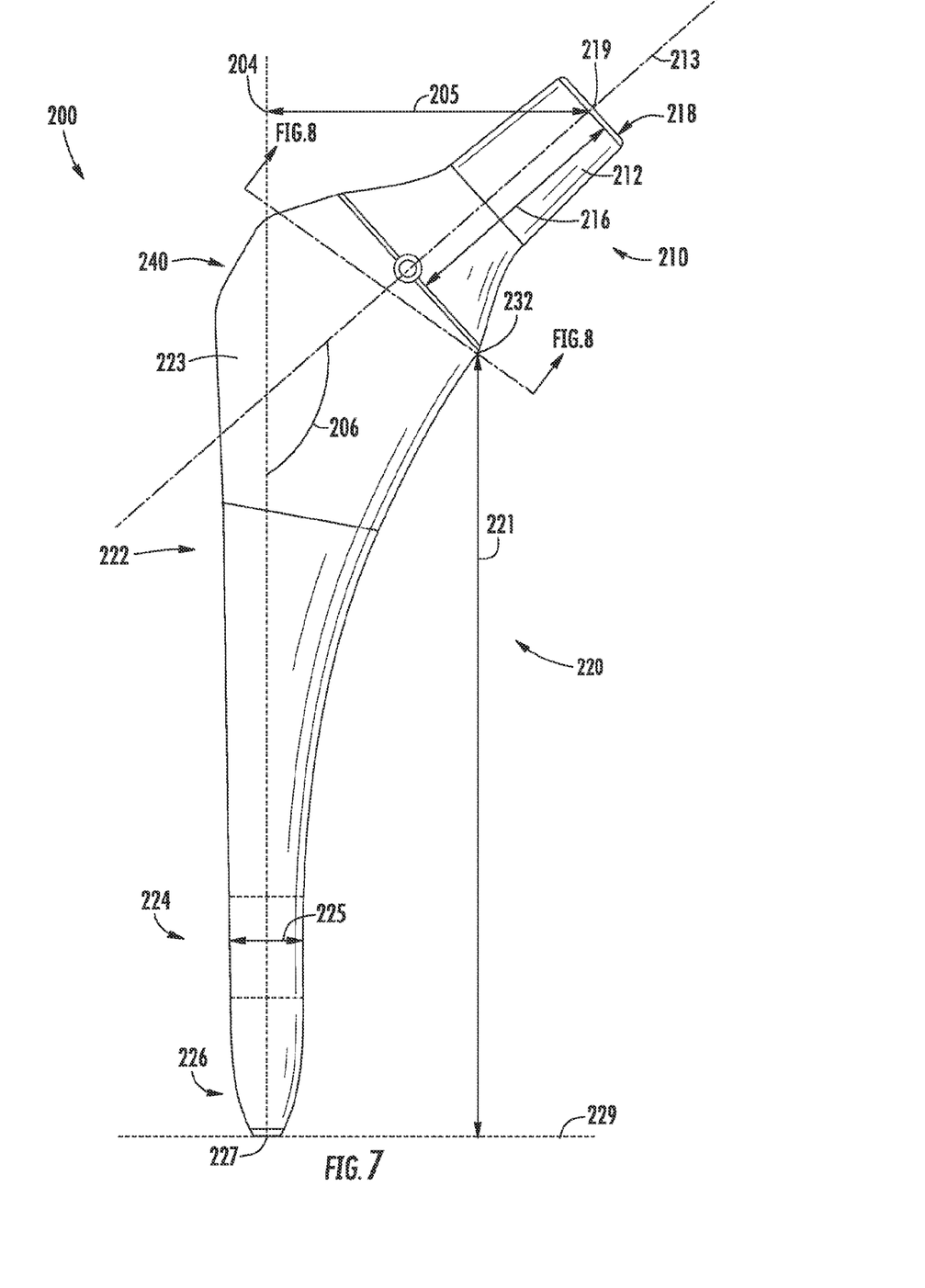
FIG. 7 is a side view of a stemmed hip implant, in accordance with some embodiments.

Referring now to FIG. 7, in some embodiments, a hip implant system can include a stemmed femoral implant 200 configured to be implanted in a femur. As with the implant 100, the femoral implant 200 can include a neck portion 210 located proximally on the femoral implant 200 and the distally located body 220 such that at least a portion of the distally located body 220 can be implanted inside a cavity that is surgically formed in a femur and the neck portion 210 can receive a ball such that the ball and attached neck portion 210 can be positioned inside the socket joint of a hip. The stemmed femoral implant 200 includes a distal stem portion 224 that is positioned within the intramedullary canal when the implant 200 is implanted in a femur.

In some embodiments, the femoral implant 200 can be configured such that use of the femoral implant in an individual is not limited based on physiologic factors of the individual such as small stature, a bowed femur, and the like. For example, the femoral implant 200 can include the body 220 with a cross-section 230 (see FIG. 8) that is small enough to be implanted in individuals with femurs that have an intramedullary canal having a smaller cross-sectional area.

TABLE 5 lists some exemplary combinations of height 234 and width 232 of the cross-section 230. It should be appreciated that other combinations of height 234 and width 232 can be used in femurs having different dimensions. In another example, the body 220 can have an overall length (described in greater detail below) that is short enough, such that when the implant 100 is placed within a surgically prepared space within a femur and/or within the intramedullary canal, the length of the body 220 does not preclude the use of the implant 200 in individuals with short femurs, bowed femurs, and the like.

Figure 9:
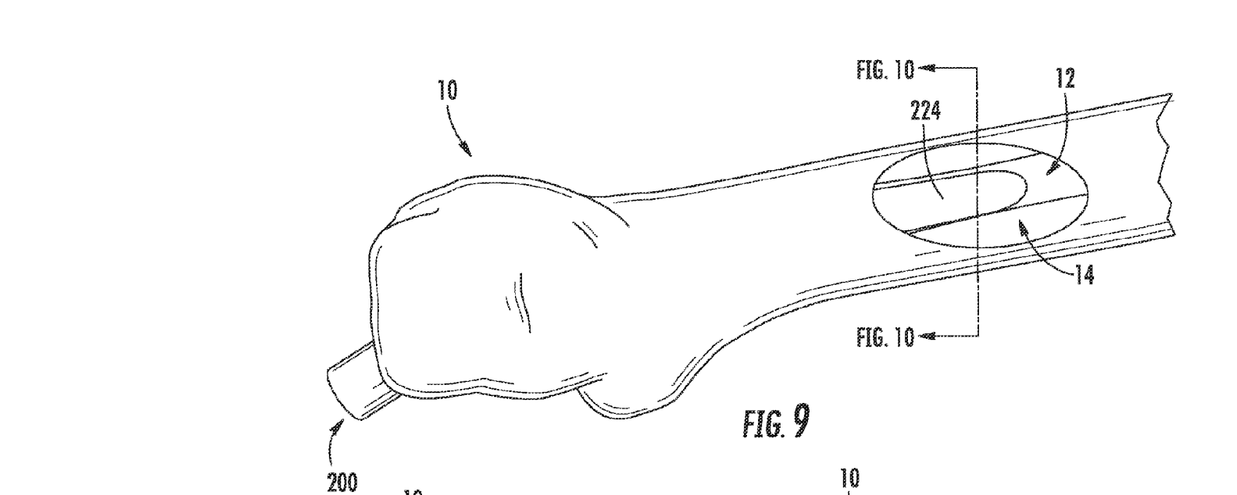
FIG. 9 is a side view of a stemmed hip implant implanted in a femur, in accordance with some embodiments.
Figure 10:
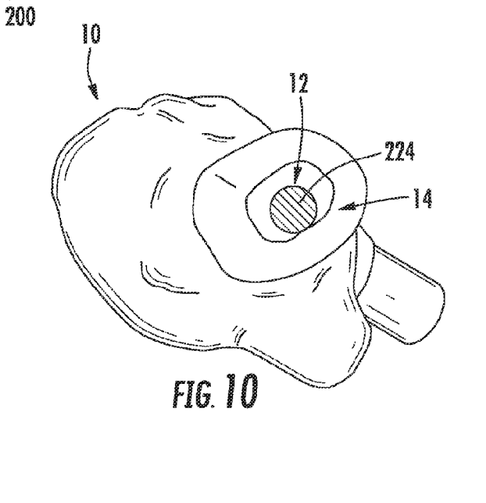
FIG. 10 is a cross-section view of the hip implant and femur of FIG. 9.
Figure 11:
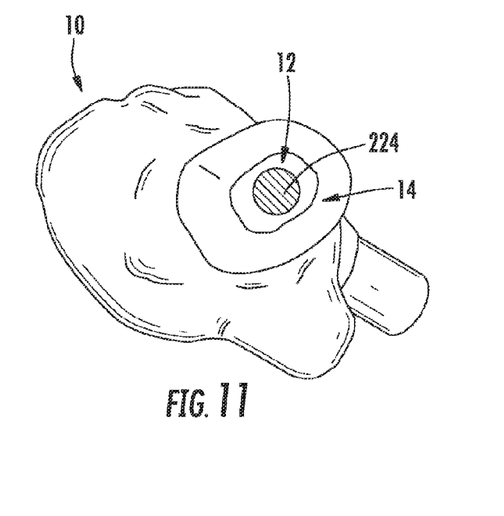
FIG. 11 is a cross-section view of a stemmed hip implant implanted in a femur where the implant stem does not contact the femur cortex, in accordance with some embodiments.

In this design, an outside stem diameter 225 of a stem portion 224 is small enough such that the stem portion 224 may not substantially contact the cortex of the intramedullary canal of the femur. In some cases, the diameter 225 can be significantly smaller than the diameter of the intramedullary canal and/or the length of the body 220 can be short enough such that the stem portion 224 can be positioned inside a bowed femur without significantly contacting the intramedullary canal cortex. Optionally, the body of the device does not substantially contact the cortex of the intramedullary canal along the full length of the body portion that is located therein the intramedullary canal. In these cases, the circumference of the body is less than the circumference of the intramedullary canal at each corresponding position from proximal to distal along the length of the body portion that is located in the intramedullary canal. Optionally, a portion of the body contacts the cortex of the intramedullary canal, but the stem portion does not substantially contact the cortex of the intramedullary canal. Insubstantial contact includes tangential contact as depicted in FIGS. 9-11.

Since the stem portion 224, or in some cases the full body portion 220, may not come into substantial contact with the cortex of the intramedullary canal, the implant's fit in the subject is less dependent on the morphology of the femoral diaphysis and can be used in conjunction with a wide range of femur morphologies. In these cases, the primary fixation of the device is provided in the metaphysis region of the patient's femur. The implant 200 can optionally be used in individuals of smaller stature, individuals with unusual morphologies, such as bowed femurs, and the like. Optionally, the device is used in patient of Asian descent.

TABLE 5

EXEMPLARY STEMMED HIP IMPLANT
DEVICE CROSS SECTION DIMENSIONS

| Device # | Height (mm) | Width (mm) |
|---|---|---|
| 1 | 26.51 | 16.96 |
| 2 | 28.28 | 18.34 |
| 3 | 30.63 | 20.42 |

The femoral implant 200 can include a proximal portion 222 of the body 220 that is tapered to allow for changes in dimension of the femur. In some embodiments, a region 223 can include a surface preparation to encourage a strengthened interface between the implant 200 and the femur it is to be implanted in. For example, the region 223 can include a porous surface substantially continuously around the outer circumference of a portion of the proximal portion 222. In some embodiments, the porous region can be applied via a plasma coating process. This process advantageously can add a porous surface (to encourage bone ingrowth and attachment) without substantially modifying or weakening the implant 200.

Figure 8:
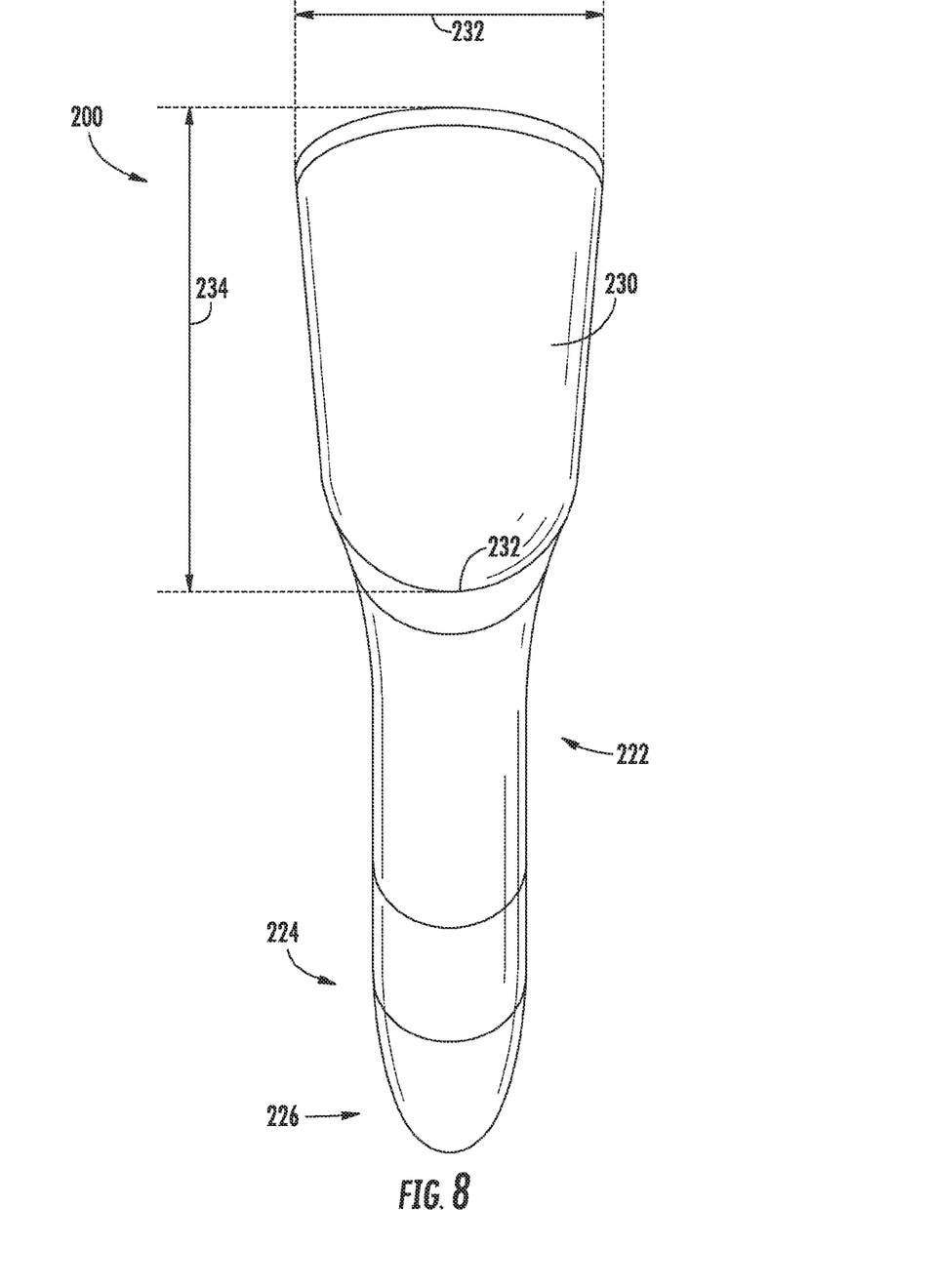
FIG. 8 is a cross-section view of the stemmed hip implant of FIG. 7.

Referring now to FIGS. 7-8, the implant 200 can include features that allow the implant 200 to be implanted in femurs exhibiting a wide array of morphologies. For example, a shorter body 220 can allow the implant 200 to be used in individuals with differently shaped femurs (e.g., shorter in length, different curvature, and the like). The implant 200 can include a lateral humped region 240 configured to accommodate implantation in femurs where more conservative resection techniques are not performed. For example, some femur resection techniques (e.g., such as those used when implanting a femur implant with a stem) involve the removal of more material than conservative techniques. For example, stems of appreciable length and bulk may not negotiate the curves of the femoral canal if inserted through a surgical resection of the femoral neck. In these cases, a portion of the superior neck and greater trochanter may be removed to allow a linear insertion that aligns the distal axis of the implant with the diaphysis of the femur. In these examples, the implant 200 can advantageously include the lateral humped region 240 that can at least partially fill the void in the superior neck and greater trochanter left during the resection. This at least partial filling of the void can lessen the likelihood of complications, such as an adverse reaction to wear debris that could otherwise migrate to the void. The implant 200 can include a neck offset 216 defined between the plane defined by the cross-section 230 and a proximal face 218 of the shaft 212. The implant 200 can be configured such that when the implant 200 is implanted in a surgically altered femur, particular dimensions can be measured from a central axis 204 defined by the stem portion 224. For example, a body offset 205 can exist between the axis 204 and a point 219 on the proximal face 218 of the shaft 212. The point 219 can be defined as the point where the axis 213 intersects the proximal face 218. In another example, the cross-section 230 can include a point 232 (see FIG. 8), on the lower portion of the cross-section 230. As such, a body length 221 can be defined as a length along a vector that is parallel to the central axis 304 and is bounded by the point 242 and a plane 229 that is perpendicular to the central axis 204 (and thus the body length 221) and contacts an outer tip 227 of the tip portion 226. Exemplary body lengths 221, neck offsets 216, and body offsets 205 can be found in TABLE 6. In some embodiments, an angle 206 of 132° can exist between the axes 204 and 213.

TABLE 6

EXEMPLARY STEMMED HIP IMPLANT
DEVICE DIMENSIONS

| Device # | Body Length (mm) | Neck Offset (mm) | Body Offset (mm) | Stem Dia (mm) |
|---|---|---|---|---|
| 1 | 80.8 | 28.9 | 33.9 | 8 |
| 2 | 91.9 | 32 | 38.2 | 8.5 |
| 3 | 97.9 | 32.3 | 39.6 | 9 |

Referring now to FIGS. 9-11, when the implant 200 is implanted in a femur 10, at least a portion of the body, for example a portion of the stem portion 224 may be positioned within the intramedullary canal 12 of the femoral diaphysis. In some embodiments, this portion of the stem 224 does not create a friction fit with the surrounding cortex. In these embodiments, the stem 224 may not contact the cortex 14, as depicted in FIG. 11, or may only tangentially contact the cortex, as depicted in FIG. 10. In some optional cases, the portions of the body that are present in the intramedullary canal do not contact the cortex to provide a friction fit.

A number of embodiments of the invention have been described. Nevertheless, it will be understood that various modifications may be made without departing from the spirit and scope of the invention. Accordingly, other embodiments are within the scope of the following claims. As used throughout the term exemplary means example. Thus, for example, and exemplary dimension is and example, or optional dimension and other examples or optional dimensions can also be used.

What is claimed is:

1. A femoral component of a hip implant device, comprising:

(a) a neck having a central axis;

(b) a body distal to the neck and having a tapered proximal portion, and a distal stem portion, the distal stem portion of the body extending to and including a distal tip portion wherein at least a portion of the distal stem portion, including the distal tip, is configured for positioning in the intramedullary canal of a subject's femur;

(c) wherein the tapered proximal portion of the body has a largest cross section perpendicular to the neck central axis, the largest cross section of the tapered proximal portion that is perpendicular to the neck central axis having a maximum height dimension and a maximum width dimension, wherein the maximum width dimension is 18.5 mm or less; and (d) wherein the largest cross section of the tapered proximal portion of the body that is perpendicular to the neck central axis is configured to be fit within at least a portion of the metaphysis of the femur when the portion of the distal stem portion, including the tip, is positioned in the intramedullary canal of the femur.

2. The femoral component of claim 1, wherein the maximum width dimension is between 15.7 mm and 18.5 mm.

3. The femoral component of claim 1, wherein the maximum height dimension is 23.9 mm or less.

4. The femoral component of claim 3, wherein the maximum height dimension is between 20.3 mm and 23.9 mm.

5. The femoral component of claim 1, wherein the tapered portion is tapered from proximal to distal end in the sagittal and coronal planes.

6. The femoral component of claim 5, wherein the tapered portion is further tapered in the lateral to medial side in cross section.

7. The femoral component of claim 1, wherein the body has an exterior surface and wherein the femoral component further comprises a porous surface coating applied circumferentially to the surface of the body.

8. The femoral component of claim 7, wherein the porous surface coating is applied by plasma spray.

9. The femoral component of claim 8, wherein the porous surface coating comprises metal.

10. The femoral component of claim 9, wherein the porous surface coating comprises titanium.

11. The femoral component of claim 7, wherein the body is titanium and wherein the porous surface coating is titanium.

12. A method of implanting a femoral component during hip surgery, comprising:
(a) providing a femoral component comprising
a neck having a central axis;
a body distal to the neck and having a tapered proximal portion, and a distal stem portion, the distal stem portion of the body extending to and including a distal tip portion wherein at least a portion of the distal stem portion, including the distal tip, is configured for positioning in the intramedullary canal of a subject's femur;
wherein the tapered proximal portion of the body has a largest cross section perpendicular to the neck central axis, the largest cross section of the tapered proximal portion that is perpendicular to the neck central axis having a maximum height dimension and a maximum width dimension, wherein the maximum width dimension is 18.5 mm or less; and
wherein the largest cross section of the tapered proximal portion of the body that is perpendicular to the neck central axis is configured to be fit within at least a portion of the metaphysis of the femur when the portion of the distal stem portion, including the tip, is positioned in the intramedullary canal of the femur; and (b) implanting the femoral component into a femur of a patient, wherein a portion of the body of the femoral component enters the intramedullary canal of the femur and wherein the portion that enters the intramedullary canal does not substantially contact the cortex of the intramedullary canal when implanted in the patient's femur.

13. The method of claim 12, wherein the portion of the body that enters the intramedullary canal has no contact with the cortex of the intramedullary canal.

14. The method of claim 12, wherein the portion of the body that enters the intramedullary canal has only tangential contact with the cortex of the intramedullary canal.

15. The method of claim 12, wherein the patient is of Asian descent.

16. The method of claim 12, wherein the femoral component is substantially fixed in the patients femur in the metaphysis of the femur.

17. A method of implanting a femoral component during hip surgery, comprising:
(a) providing a femoral component comprising
a neck having a central axis;
a body distal to the neck and having a tapered proximal portion, and a distal stem portion, the distal stem portion of the body extending to and including a distal tip portion wherein at least a portion of the distal stem portion, including the distal tip, is configured for positioning in the intramedullary canal of a subject's femur;
wherein the tapered proximal portion of the body has a largest cross section perpendicular to the neck central axis, the largest cross section of the tapered proximal portion that is perpendicular to the neck central axis having a maximum height dimension and a maximum width dimension, wherein the maximum width dimension is 18.5 mm or less; and
wherein the largest cross section of the tapered proximal portion of the body that is perpendicular to the neck central axis is configured to be fit within at least a portion of the metaphysis of the femur when the portion of the distal stem portion, including the tip, is positioned in the intramedullary canal of the femur; and (b) implanting the femoral component into a femur of a patient, wherein a portion of the body, including the distal stem portion, of the femoral component enters the intramedullary canal of the femur and wherein the distal stem portion does not substantially contact the cortex of the intramedullary canal when the femoral component is implanted in the patient's femur.

18. The method of claim 17, wherein the portion of the body that enters the intramedullary canal has no contact with the cortex of the intramedullary canal.

19. The method of claim 17, wherein the portion of the body that enters the intramedullary canal has only tangential contact with the cortex of the intramedullary canal.

20. The method of claim 17, wherein the patient is of Asian descent.

21. The method of claim 17, wherein the femoral component is substantially fixed in the patients femur in the metaphysis of the femur.

* * * * *